United States Patent
Kehres et al.

(10) Patent No.: US 12,220,321 B2
(45) Date of Patent: *Feb. 11, 2025

(54) AUGMENTED GLENOID WITH GROOVE

(71) Applicant: Biomet Manufacturing, LLC, Warsaw, IN (US)

(72) Inventors: Clinton E. Kehres, Warsaw, IN (US); Michael Francis Kovacs, Winona Lake, IN (US); Thomas Michael Vanasse, Gainesville, FL (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/975,767

(22) Filed: Oct. 28, 2022

(65) Prior Publication Data
US 2023/0050551 A1    Feb. 16, 2023

Related U.S. Application Data

(63) Continuation of application No. 15/496,958, filed on Apr. 25, 2017, now Pat. No. 11,510,785.

(51) Int. Cl.
*A61F 2/40*  (2006.01)
*A61F 2/30*  (2006.01)

(52) U.S. Cl.
CPC .............. *A61F 2/4081* (2013.01); *A61F 2/30* (2013.01); *A61F 2/40* (2013.01); *A61F 2002/30487* (2013.01); *A61F 2002/30736* (2013.01); *A61F 2002/3082* (2013.01); *A61F 2002/30878* (2013.01); *A61F 2002/30881* (2013.01); *A61F 2002/4085* (2013.01); *A61F 2310/00011* (2013.01)

(58) Field of Classification Search
None
See application file for complete search history.

(56) References Cited

U.S. PATENT DOCUMENTS 5,723,018 A * 3/1998 Cyprien .................... A61F 2/40
                                                   623/19.13
5,800,551 A    9/1998 Williamson et al.
(Continued)

FOREIGN PATENT DOCUMENTS

CN    101980671 A    2/2011
CN    102883672 A    1/2013
(Continued)

OTHER PUBLICATIONS

"U.S. Appl. No. 15/496,958, Advisory Action mailed Jun. 19, 2020", 3 pgs.
(Continued)

*Primary Examiner* — Ann Schillinger
(74) *Attorney, Agent, or Firm* — Schwegman Lundberg & Woessner, P.A.

(57) ABSTRACT

Disclosed herein is an implant. The implant can include a body and a plurality of fixation members. The body can define an articular surface and a bone engaging surface opposite the articular surface. The bone engaging surface can define a groove that separates a first section of the bone engaging surface from a second section of the bone engaging surface. The plurality of fixation members can extend from the bone engaging surface.

18 Claims, 12 Drawing Sheets

(56) References Cited

U.S. PATENT DOCUMENTS

| | | | |
|---|---|---|---|
| 5,876,447 A | 3/1999 | Arnett | |
| 6,699,289 B2* | 3/2004 | Iannotti | A61B 17/1684 623/19.13 |
| 6,896,702 B2* | 5/2005 | Collazo | A61F 2/389 623/20.16 |
| 6,911,047 B2* | 6/2005 | Rockwood, Jr. | A61F 2/4081 128/898 |
| 7,892,287 B2* | 2/2011 | Deffenbaugh | A61F 2/4081 623/19.11 |
| 8,080,063 B2* | 12/2011 | Ferrand | A61F 2/4081 623/19.13 |
| 8,465,548 B2* | 6/2013 | Long | A61F 2/4081 623/19.11 |
| 8,480,750 B2* | 7/2013 | Long | A61F 2/40 623/19.11 |
| 8,540,778 B2 | 9/2013 | Rhodes et al. | |
| 8,556,901 B2* | 10/2013 | Anthony | A61B 17/1735 606/177 |
| 8,778,028 B2 | 7/2014 | Gunther et al. | |
| 9,414,927 B2 | 8/2016 | Iannotti et al. | |
| 9,955,984 B2 | 5/2018 | Winslow et al. | |
| 10,028,838 B2 | 7/2018 | Hodorek et al. | |
| 10,258,478 B2* | 4/2019 | Kovacs | A61F 2/4081 |
| 10,624,755 B2* | 4/2020 | Amis | A61F 2/4081 |
| 10,722,374 B2* | 7/2020 | Hodorek | A61F 2/4081 |
| 11,510,785 B2* | 11/2022 | Kehres | A61F 2/40 |
| 2004/0059424 A1* | 3/2004 | Guederian | A61B 17/864 623/19.11 |
| 2006/0069443 A1* | 3/2006 | Deffenbaugh | A61F 2/4081 623/19.11 |
| 2006/0122705 A1 | 6/2006 | Morgan | |
| 2007/0055380 A1* | 3/2007 | Berelsman | A61F 2/4612 623/908 |
| 2007/0142917 A1* | 6/2007 | Roche | A61F 2/4081 623/23.43 |
| 2007/0179624 A1* | 8/2007 | Stone | A61F 2/4081 623/22.36 |
| 2007/0244564 A1 | 10/2007 | Ferrand et al. | |
| 2008/0133020 A1 | 6/2008 | Blackwell et al. | |
| 2008/0188940 A1 | 8/2008 | Cohen et al. | |
| 2011/0035013 A1* | 2/2011 | Winslow | A61F 2/4081 623/19.13 |
| 2011/0118846 A1* | 5/2011 | Katrana | A61F 2/4059 623/19.13 |
| 2012/0130499 A1 | 5/2012 | Long | |
| 2013/0261753 A1* | 10/2013 | Lappin | A61F 2/30734 623/19.11 |
| 2013/0304226 A1 | 11/2013 | Ritz et al. | |
| 2014/0031945 A1* | 1/2014 | Baptista | A61F 2/4081 623/19.11 |
| 2015/0150688 A1* | 6/2015 | Vanasse | G06T 17/00 703/1 |
| 2015/0272741 A1* | 10/2015 | Taylor | A61F 2/4081 623/19.11 |
| 2015/0374502 A1* | 12/2015 | Hodorek | A61B 17/1684 606/80 |
| 2016/0045323 A1 | 2/2016 | Kovacs et al. | |
| 2016/0151164 A1* | 6/2016 | Taylor | A61F 2/30734 623/19.11 |
| 2016/0324649 A1* | 11/2016 | Hodorek | A61F 2/4081 |
| 2016/0367375 A1* | 12/2016 | Boulris | A61B 17/1684 |
| 2017/0172764 A1* | 6/2017 | Muir | A61F 2/4014 |
| 2018/0271668 A1 | 9/2018 | Kemp et al. | |
| 2018/0303619 A1 | 10/2018 | Kehres et al. | |

FOREIGN PATENT DOCUMENTS

| | | |
|---|---|---|
| CN | 103702627 A | 4/2014 |
| CN | 104042367 A | 9/2014 |
| CN | 104755047 A | 7/2015 |
| CN | 204814288 U | 12/2015 |
| CN | 105377195 A | 3/2016 |
| CN | 105853027 A | 8/2016 |
| CN | 106456336 A | 2/2017 |
| CN | 110545760 A | 12/2019 |
| EP | 2335655 A1 | 6/2011 |
| EP | 2962650 A1 | 1/2016 |
| WO | WO-2018200101 A1 | 11/2018 |

OTHER PUBLICATIONS

"U.S. Appl. No. 15/496,958, Advisory Action mailed Dec. 21, 2021", 3 pgs.

"U.S. Appl. No. 15/496,958, Examiner Interview Summary mailed Jan. 14, 2020", 3 pgs.

"U.S. Appl. No. 15/496,958, Examiner Interview Summary mailed Mar. 11, 2019", 3 pgs.

"U.S. Appl. No. 15/496,958, Examiner Interview Summary mailed Jun. 18, 2021", 2 pgs.

"U.S. Appl. No. 15/496,958, Final Office Action mailed Jan. 10, 2019", 11 pgs.

"U.S. Appl. No. 15/496,958, Final Office Action mailed Apr. 15, 2020", 18 pgs.

"U.S. Appl. No. 15/496,958, Final Office Action mailed Oct. 13, 2021", 10 pgs.

"U.S. Appl. No. 15/496,958, Non Final Office Action mailed Apr. 22, 2021", 10 pgs.

"U.S. Appl. No. 15/496,958, Non Final Office Action mailed Jul. 6, 2018", 8 pgs.

"U.S. Appl. No. 15/496,958, Non Final Office Action mailed Nov. 13, 2019", 11 pgs.

"U.S. Appl. No. 15/496,958, Notice of Allowance mailed Jul. 27, 2022", 11 pgs.

"U.S. Appl. No. 15/496,958, Response filed Jan. 10, 2020 to Non Final Office Action mailed Nov. 13, 2019", 12 pgs.

"U.S. Appl. No. 15/496,958, Response filed Jun. 15, 2020 to Final Office Action mailed Apr. 15, 2020", 16 pgs.

"U.S. Appl. No. 15/496,958, Response filed Jun. 20, 2018 to Restriction Requirement mailed May 29, 2018".

"U.S. Appl. No. 15/496,958, Response filed Jun. 28, 2018 to Restriction Requirement mailed May 29, 2018", 6 pgs.

"U.S. Appl. No. 15/496,958, Response filed Jul. 9, 2021 to Non Final Office Action mailed Apr. 22, 2021", 14 pgs.

"U.S. Appl. No. 15/496,958, Response filed Sep. 14, 2018 to Non-Final Office Action Mailed Jul. 6, 2018", 14 pgs.

"U.S. Appl. No. 15/496,958, Response filed Dec. 9, 2021 to Final Office Action mailed Oct. 13, 2021", 11 pgs.

"U.S. Appl. No. 15/496,958, Response filed Mar. 27, 2019 to Final Office Action mailed Jan. 10, 2019", 13 pgs.

"U.S. Appl. No. 15/496,958, Restriction Requirement mailed May 29, 2018", 8 pgs.

"Chinese Application Serial No. 201880027116.0, Office Action mailed May 26, 2021", (W/English Translation), 15 pgs.

"Chinese Application Serial No. 201880027116.0, Response filed Sep. 6, 2021 to Office Action mailed May 26, 2021", with English claims, 11 pages.

"European Application Serial No. 18716472.8, Response to Communication pursuant to Rules 161(1) and 162 EPC filed Jun. 30, 2020", 12 pgs.

"International Application Serial No. PCT/US2018/023729, International Preliminary Report on Patentability mailed Nov. 7, 2019", 8 pgs.

"International Application Serial No. PCT/US2018/023729, International Search Report mailed Jun. 28, 2018", 6 pgs.

"International Application Serial No. PCT/US2018/023729, Written Opinion mailed Jun. 28, 2018", 6 pgs.

U.S. Appl. No. 15/496,958, filed Apr. 25, 2017, Augmented Glenoid With Groove.

* cited by examiner

AUGMENTED GLENOID WITH GROOVE

CLAIM OF PRIORITY

This application is a continuation of U.S. patent application Ser. No. 15/496,958, filed on Apr. 25, 2017, the benefit of priority of which is claimed hereby, and which is incorporated by reference herein in its entirety.

FIELD OF THE DISCLOSURE

The present disclosure relates to surgical implant systems, including implants, instruments, and methods for installing an implant. Specifically, the present disclosure relates to systems and methods for implanting an augmented glenoid.

BACKGROUND

Surgical procedures for repairing or reconstructing a joint can require securely fastening a surgical implant to a bone. For example, shoulder joint reconstruction can require fixing a glenoid implant to a scapula to reproduce or replicate a glenoid cavity on the scapula. The surgical implant can be securely fastened to the bone in a variety of ways, including mechanical fasteners and bone cement.

SUMMARY

To better illustrate the system disclosed herein, a non-limiting list of examples is provided here:

Example 1 can include an implant. The implant can comprise a body and a plurality of fixation members. The body can define an articular surface and a bone engaging surface opposite the articular surface. The bone engaging surface can define a groove that separates a first section of the bone engaging surface from a second section of the bone engaging surface. The plurality of fixation members can extend from the bone engaging surface.

In Example 2, the implant of Example 1 can optionally include the groove having a curved profile.

In Example 3, the implant of Example 1 can optionally include the groove having a rectangular profile.

In Example 4, the implant of any one of or any combination of Examples 1-3 can optionally include the groove following a curved path defined by an intersection of the first section of the bone engaging surface and the second section of the bone engaging surface.

In Example 5, the implant of any one of or any combination of Examples 1-4 can optionally include a boss extending from the bone engaging surface. The boss can divide the groove into a first portion and a second portion.

In Example 6, the implant of Example 5 can optionally include the first portion of the groove having a different profile than the second portion of the groove.

In Example 7, the implant of any one of or any combination of Examples 1-6 can optionally include the groove including a porous metal surface.

In Example 8, the implant of any one of or any combination of Examples 1-7 can optionally include the first section of the bone engaging surface and the second surface of the bone engaging surface defining an angle.

In Example 9, the implant of Example 8 can optionally include: the angle being between about 5 degrees and about 20 degrees.

In Example 10, the implant of any one of or any combination of Examples 1-9 can optionally include a first edge defined by an intersection of the first section of the bone engaging surface and the groove including a first relief and a second edge defined by an intersection of the second section of the bone engaging surface and the groove including a second relief.

In Example 11, the implant of Example 10 can optionally include the first relief having a first profile and the second relief having a second profile. The first profile can be similar to the second profile.

In Example 12, the implant of Example 10 can optionally include the first relief having a first profile and the second relief having a second profile. The first profile can be different from the second profile.

In Example 13, the implant of Example 10 can optionally include the first relief and the second relief each having a rounded profile.

In Example 14, the implant of Example 10 can optionally include the first relief and the second relief each having a chamfered profile.

Example 15 can include a glenoid implant. The glenoid implant can comprise an articular surface, a first scapular engaging surface, and a second scapula engaging surface. The first scapula engaging surface can be opposite the articular surface. The second scapula engaging surface can be opposite the articular surface. The first scapula engaging surface and the second scapula engaging surface can be separated by a curved surface sized to receive an irregularity defined by a first reamed scapula surface and a second reamed scapula surface.

In Example 16, the glenoid implant of Example 15 can optionally include the curved surface following a curved path separating the first scapula engaging surface and the second scapula engaging surface.

In Example 17, the glenoid implant of Example 15 and 16 can optionally include a boss extending from a portion of each of the first scapula engaging surface and the second scapula engaging surface. The boss can divide the curved surface into a first portion and a second portion.

In Example 18, the glenoid implant of Example 17 can optionally include the first portion of the curved surface having a different profile than the second portion of the curved surface.

In Example 19, the glenoid implant of any one of or any combination of Examples 15-18 can optionally include a porous metal layer located adjacent to at least one of the curved surface, the first scapula engaging surface, and the second scapula engaging surface.

In Example 20, the glenoid implant of any one of or any combination of Examples 15-19 can optionally include the first scapula engaging surface extending along a first plane and the second scapula engaging surface extending along a second plane. The first and second planes can intersect to define an angle.

In Example 21, the glenoid implant of Example 20 can optionally include the angle being between about 5 degrees and about 20 degrees.

In Example 22, the glenoid implant of any one of or any combination of Examples 15-21 can optionally include a first edge defined by an intersection of the first scapula engaging surface and the curved surface including a first relief and a second edge defined by an intersection of the second scapula engaging surface and the curved surface including a second relief.

In Example 23, the glenoid implant of Example 22 can optionally include the first relief having a first profile and the second relief having a second profile. The first profile can be similar to the second profile.

In Example 24, the glenoid implant of Example 22 can optionally include the first relief having a first profile and the second relief having a second profile. The first profile can be different from the second profile.

In Example 25, the glenoid implant of Example 22 can optionally include the first relief and the second relief each having a rounded profile.

In Example 26, the glenoid implant of Example 22 can optionally include the first relief and the second relief each having a chamfered profile.

Example 27 can include a method for implanting a glenoid implant. The method can comprise: reaming a scapula to define a first scapula surface and a second scapula surface, the first scapula surface and the second scapula surface intersecting at an irregularity; and implanting the glenoid implant such that a first scapula engaging surface of the glenoid implant contacts the first scapula surface, a second scapula engaging surface of the glenoid implant contacts the second scapula surface, and an groove in the glenoid implant separating the first scapula engaging surface and the second scapula engaging surface at least partially receives the irregularity therein.

In Example 28, the method of Example 27 can optionally include applying bone cement to at least one of the groove and the irregularity prior to implanting the glenoid implant.

In Example 29, the implant or methods of any one of or any combination of Examples 1-28 is optionally configured such that all elements or options recited are available to use or select from.

BRIEF DESCRIPTION OF THE FIGURES

The above-mentioned and other features and advantages of this disclosure, and the manner of attaining them, will become more apparent and the disclosure itself will be better understood by reference to the following description of embodiments taken in conjunction with the accompanying drawings, wherein.

Corresponding reference characters indicate corresponding parts throughout the several views. The exemplifications set out herein illustrate exemplary embodiments of the disclosure, and such exemplifications are not to be construed as limiting the scope of the disclosure any manner.

DETAILED DESCRIPTION

Figure 1A:
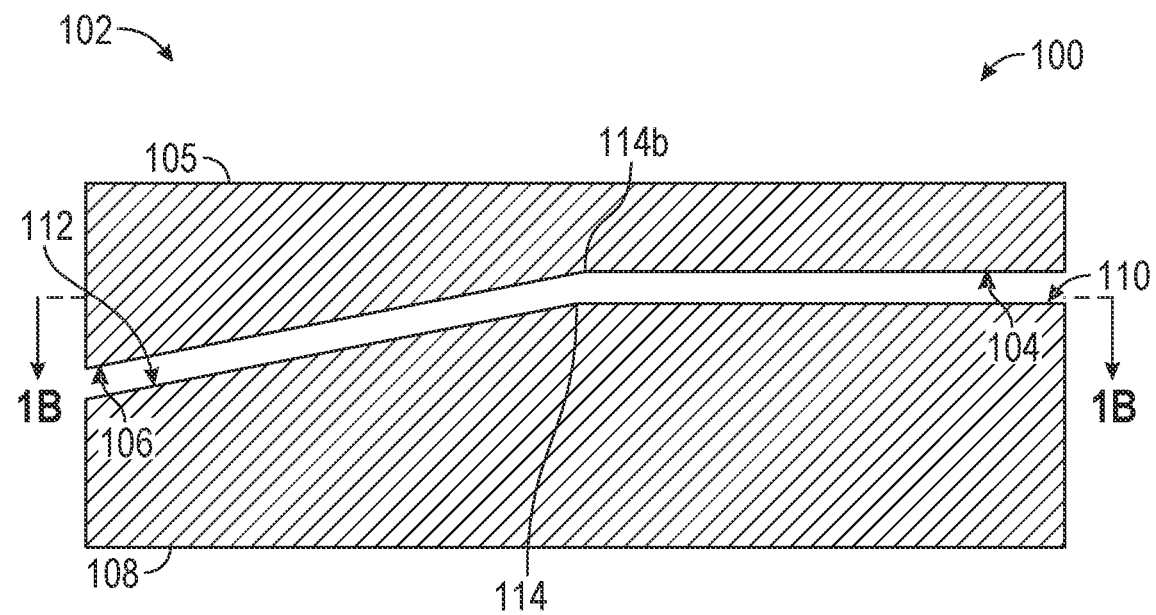
FIGS. 1A, 1B, 1C, and 1D show schematic views of an augment scapula interface.

As used herein, the following directional definitions apply. Anterior and posterior mean nearer the front or nearer the rear of the body, respectively, proximal and distal mean nearer to or further from the root of a structure, respectively, and medial and lateral mean nearer the sagittal plane or further from the sagittal plane, respectively. The sagittal plane is an imaginary vertical plane through the middle of the body that divides the body into right and left halves. In addition, the terms implant and prosthesis, and variations thereof, can be used interchangeably.

Through injury, trauma, aging, or other degenerative conditions a joint, such as the shoulder, can become damaged or otherwise less mobile. In addition, the injury, trauma, aging, or other condition can cause repeated injury. For example, an injury to a shoulder can cause a central defect or other damage to a glenoid. The damage can cause the humeral head to more easily become dislocated from the glenoid, limit range of motion, cause pain during motion, etc.

As disclosed herein, a glenoid implant can have an augment that can be used to replace damaged or diseased bone. The glenoid implant can include an articulating surface and a bone-engaging surface and the augment can form a portion of the bone engaging surface. In a particularly novel and inventive aspect, the bone-engaging surface on the glenoid implant can include a groove that is formed between two sections of the implant, viz., an augment side and a non-augment side. The groove can be sized to receive a portion of a reamed bone, such as a vertex where two "sides" of bone meet. The two sides of bone interface with, and correspond to, the augment side and non-augment side of the glenoid implant. The two sides of bone can be reamed to form a "negative" or mating surface with respect to the bone-engaging surface of the glenoid implant. For example, during a shoulder replacement, a scapula can be reamed such that two surfaces of the scapula form a vertex. During surgery, a surgeon can position the glenoid implant such that the vertex rests within the groove on the bone-engaging side of the implant. The "vertex" can comprise the portion of bone where two or more reamed bone surfaces intersect. Reaming the glenoid portion of a scapula may not be done perfectly such that the bone surfaces do not correspond exactly to the bone-engaging surface of the glenoid. Reaming can often result in irregularities, such as an offset vertex, an irregular line or curve along the glenoid bone, a rounded edge along the vertex as opposed to a sharp, clean edge, a protrusion where a portion of one or both sides of the bone extends away from the bone, or any other "irregularity" where the bone does not correspond to a shape of the bone-engaging surface of the glenoid due to imperfections in reaming, for example.

To accommodate such irregularities, a groove can be formed on the bone-engaging side of the glenoid implant. Having irregularities reside within the groove provides some flexibility in reaming and preciseness in placing the glenoid implant by allowing the glenoid implant to sit flush on the prepared glenoid bone.

Figure 1B:
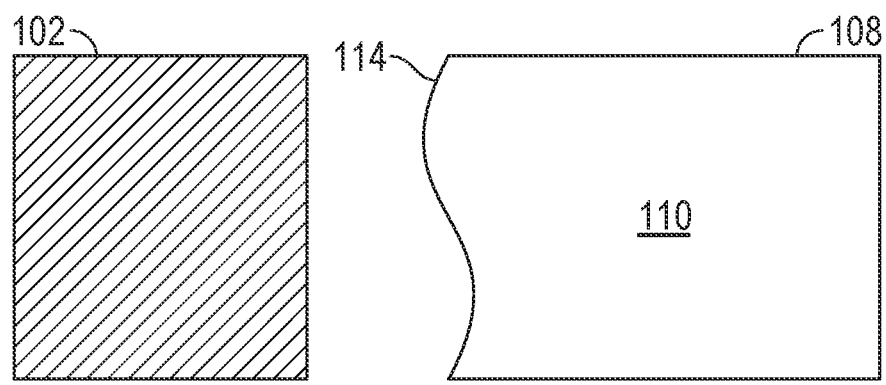
Figure 1C:
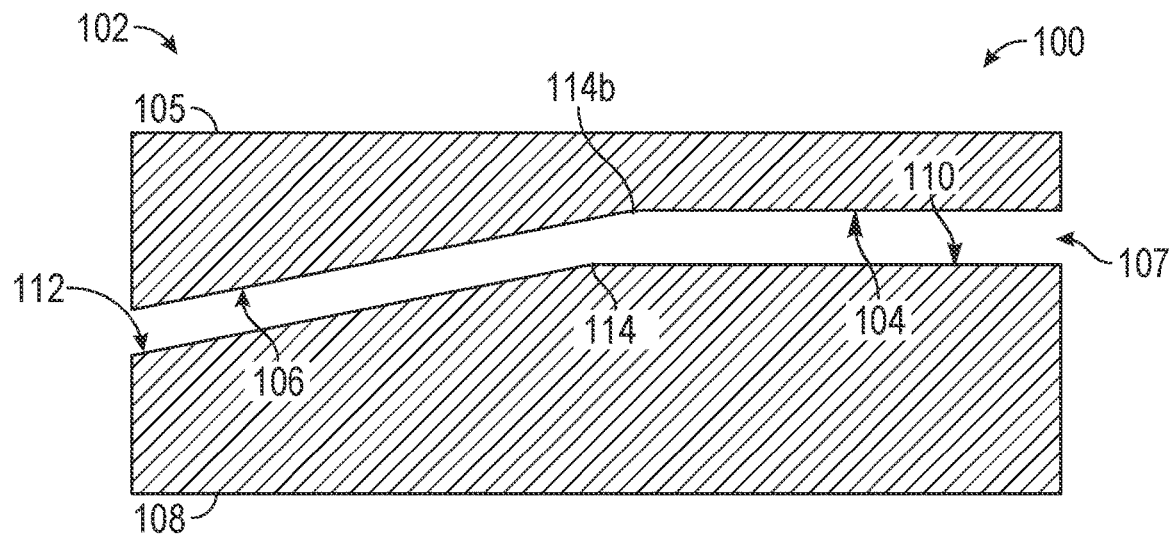
Figure 1D:
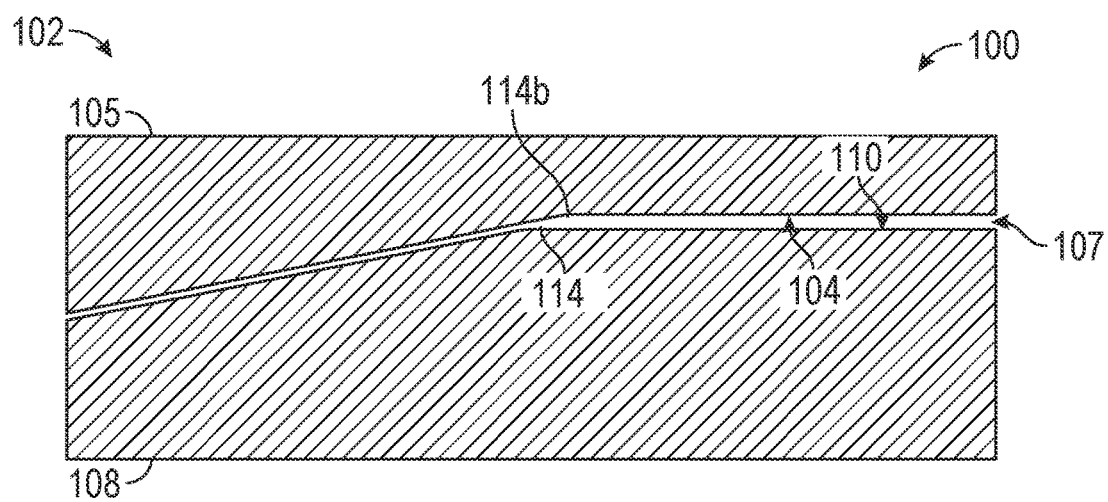

FIGS. 1A, 1B, 1C, and 1D show a simple schematic 100 of an implant-scapula interface. As shown in FIGS. 1A, 1C, and 1D, an implant 102 can include a first bone-engaging surface 104, a second bone-engaging surface 106, and an augment 105 on the left side of the implant 102 in FIG. 1A, A bone 108 can include a first bone surface 110 and a second bone surface 112, where the first bone surface 110 has been reamed to have a flat, planar surface, and the second bone surface 112 has been reamed to have a flat, planar surface at an angle with respect to the first bone surface 110.

The first bone surface 110 and the second bone surface 112 can form a vertex 114, which may have one or more irregularities, as discussed above, such as being offset, to the left, or right in at least a portion of the vertex 114 when compared to a desired location of the vertex 114. The vertex 114 can be formed during a reaming process that also forms the first bone surface 110 and the second bone surface 112. As shown in FIG. 1B to a somewhat exaggerated extent, the vertex 114 can contain irregularities such as an undesired curve along vertex 114. Stated another way, due to possible movement of the bone 108, reaming guide, or reamer, or other conditions in the operating room, the vertex 114 may not be formed with a desired preciseness.

The irregularities in vertex 114 can cause unwanted gaps or spaces, such as space 107 shown in FIGS. 1C and 1D) between the first bone surface 110 and the first bone engaging surface 104 and/or the second bone surface 112 and the second bone engaging surface 106. Such gaps can cause rocking of the glenoid implant because the implant does not sit flush against the reamed bone, as shown in FIGS. 1C and 1D. Upon securing the implant to the bone, the implant may be at an improper angle due to such gaps 107. The unwanted gaps can be caused by the vertex 114 not conforming to a particular shape, such as a linear or otherwise sharp edge that can be formed by the intersection of the first bone engaging surface 104 and the second bone engaging surface 106. Other particular shapes may be desired for the vertex 114, such as having one or more curves or one or more slopes along a length of vertex 114. But in any case, the vertex 114 is meant to correspond to a vertex 114b on the glenoid implant where the augment side and the non-augment side of the bone-engaging surface intersect, or in the case of the present disclosure, to fall within a groove formed on the bone-engaging surface of the implant.

Figure 2A:
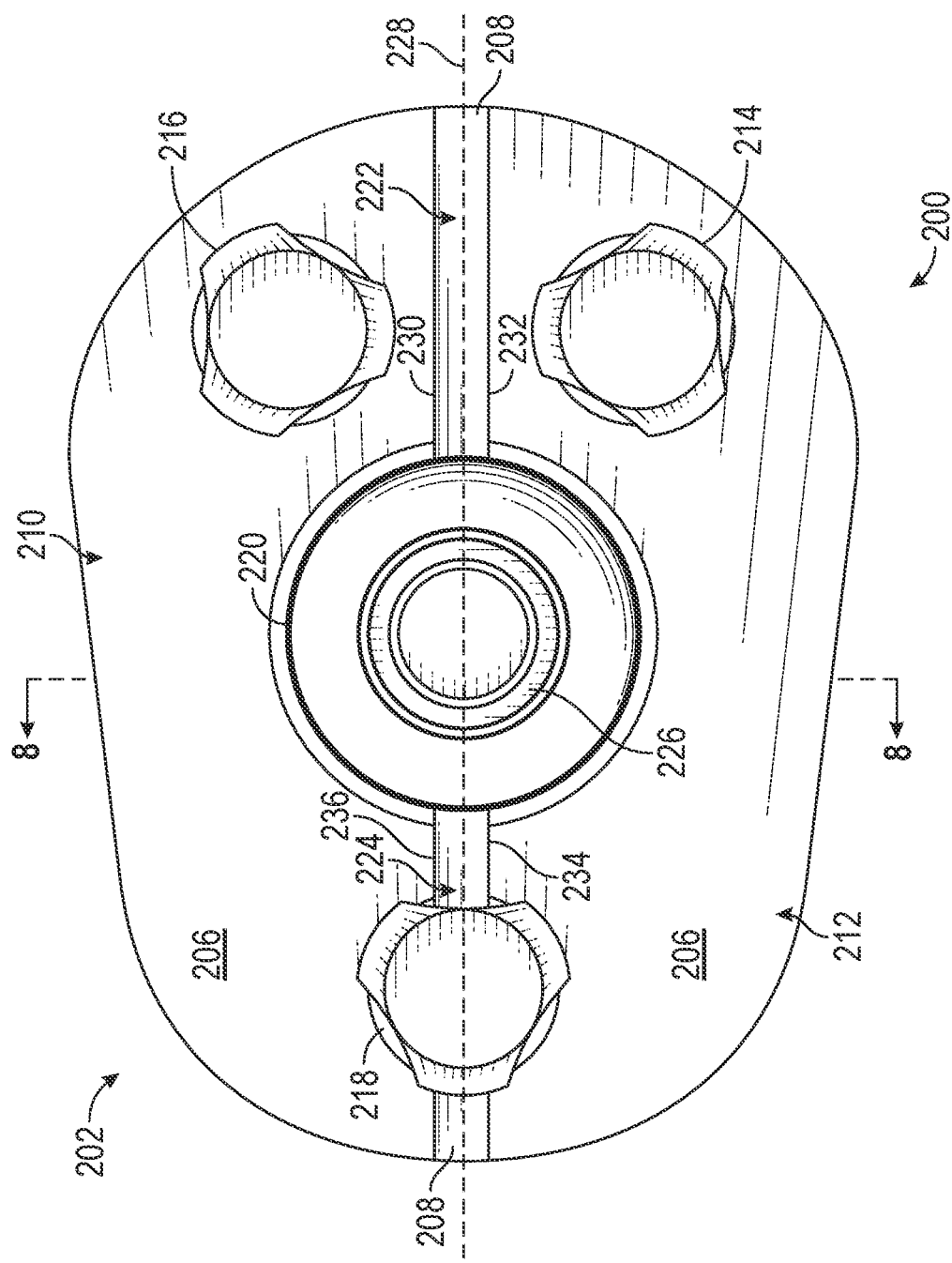
FIGS. 2A, 2B, and 2C show a glenoid implant in accordance with at least one example of the present disclosure.
Figure 2B:
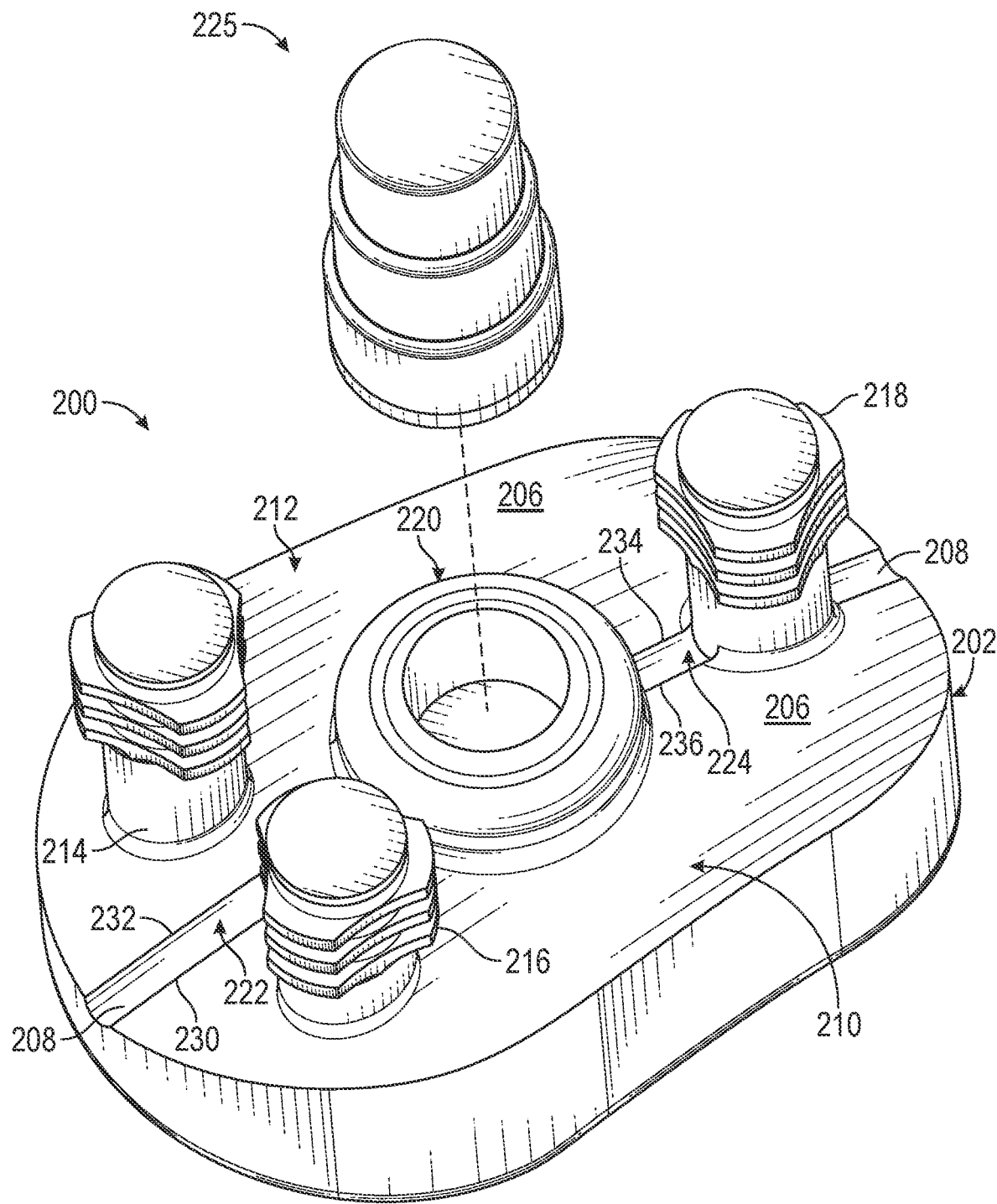
Figure 2C:
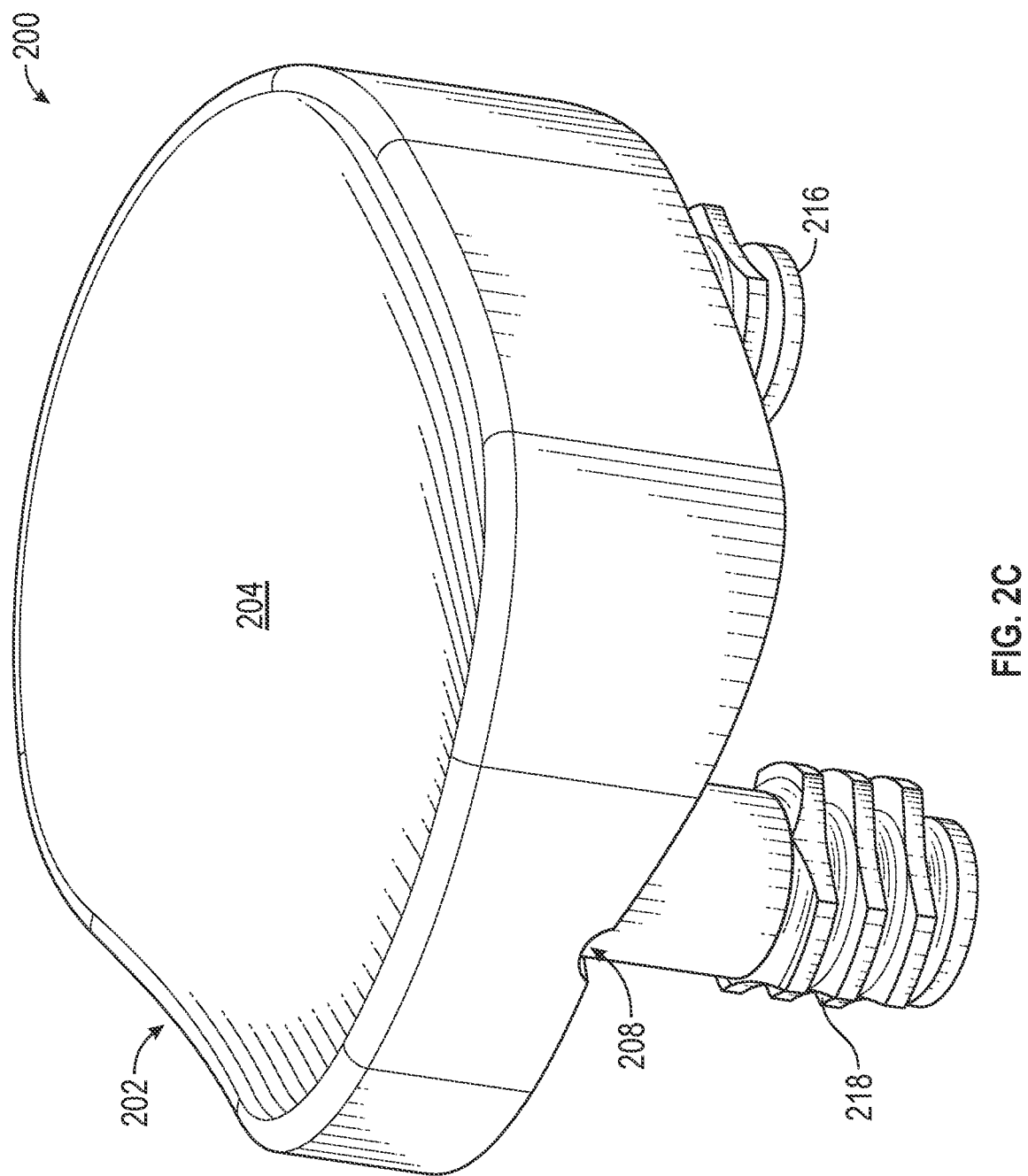

FIGS. 2A, 2B, and 2C show views of a glenoid implant 200 in accordance with at least one example of the present disclosure. As shown in FIGS. 2A, 2B, and 2C, the glenoid implant 200 can include a body 202 that defines an articulation surface 204 (FIG. 2C) and a bone-engaging surface 206. A groove 208 can separate the bone-engaging surface 206 into a first section 210 and a second section 212. Either the first section 210 or the second section 212 can be augmented, or raised, with respect to the other section 210/212. One or more fixation pegs, such as a first fixation peg 214, a second fixation peg 216, and a third fixation peg 218, can extend from the bone-engaging surface 206. The glenoid implant 200 in FIGS. 2A-2C shows three fixation pegs, but the glenoid implant 200 can have two fixation pegs in a linear arrangement with respect to a central peg or boss 220.

The glenoid implant 200 can also include at least one boss 220 that is threaded or tapered, for example, to secure a central peg 225 thereto. Alternatively, boss 220 can comprise an inset that is threaded or tapered to secure a central peg to the bone-engaging surface 206. The central peg can be shaped similar to the fixation pegs or have a different shape. The boss 220 can divide the groove 208 into a first section 222 and second section 224. In addition, as shown, a fixation peg, such as the third fixation peg 218, can further divide the groove 208 as well. In arrangements where the fixation pegs are arranged in a linear arrangement, each of the fixation pegs can similarly divide the groove 208.

Groove 208 can allow for a concavity to be formed between the first section 210 and the second section 212. During implantation of the glenoid implant 200, irregularities within the vertex 114 can rest within the groove 208 and allow the bone-engaging surface 206 to better contact and sit flush against the bone surfaces 110 and 112.

Figure 3A:
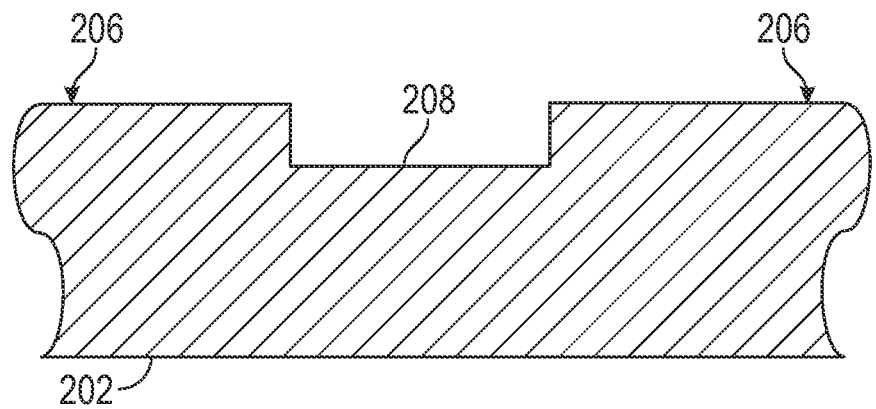
FIGS. 3A and 3B show a groove in accordance with at least one example of the present disclosure.
Figure 3B:
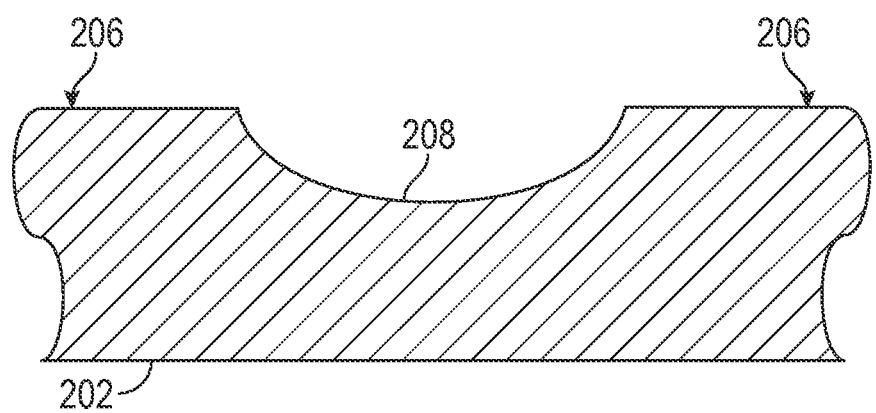

Groove 208 can be a groove or a channel having sides thereto along its length (e.g., curved or straight sides). It should be appreciated that groove 208 is not planar; in other words, it does form a merely flat interface between first section 210 and second section 212. In addition, groove 208 can have a circular profile as shown in FIGS. 2A, 2B, and 2C. The groove 208 can also have, for example, a rectangular (see FIG. 3A), oblong or elliptical profile (see FIG. 3B). Furthermore, various sections of the groove 208 can include differing profiles. For example, the first section 222 can have a circular profile and the second section 224 can have a rectangular profile. Similarly, all or different portions of groove 208 can be sloped with respect to other portions of groove 208.

Figure 4:
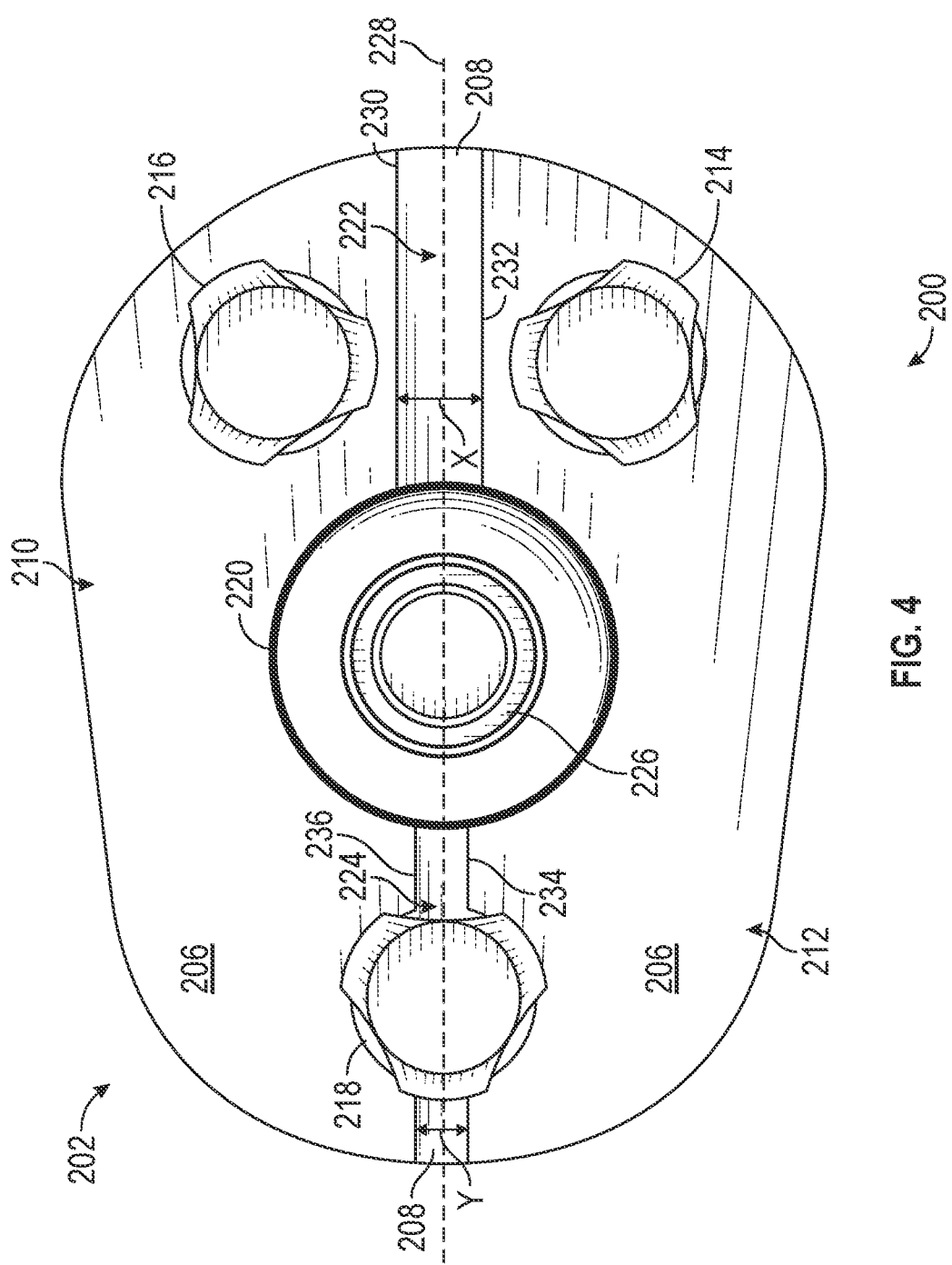
FIG. 4 shows a glenoid implant in accordance with at least one example of the present disclosure.

The width and depth of groove 208 can vary. For example, as shown in FIG. 4, the first section 222 can be circular and have a width Y or a diameter of Y and the second section 224 can be circular and have a width X or a diameter of X. Width and diameter of groove 208 need not correspond to or equal each other. Furthermore, the size of the groove 208 can vary along its path of travel. For instance, a portion of the groove 208 proximate the third fixation peg 218 can have a width X or diameter X and a portion of the groove 208 proximate the first fixation peg 214 and second fixation peg 216 can have a width Y or diameter Y. The width or diameter of the groove 208 can increase linearly or non-linearly from X to Y along the path of the groove 208.

Figure 5:
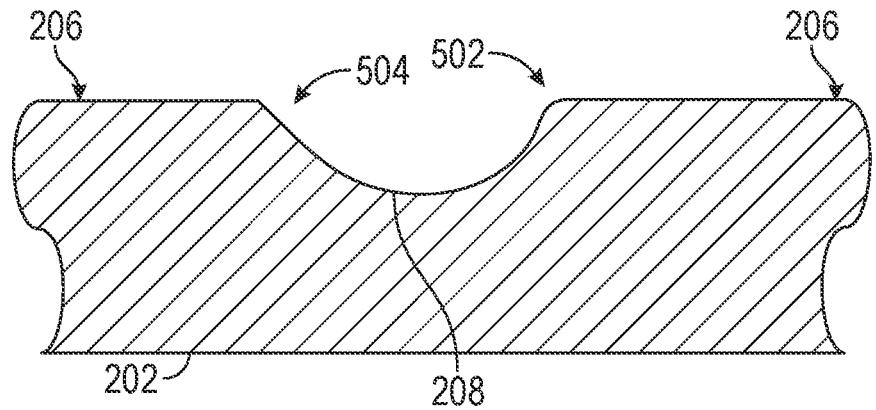
FIG. 5 shows reliefs in in accordance with at least one example of the present disclosure.

An intersection of the groove 208 and the bone engaging surface 206 can form edges 230, 232, 234, and 236. The edges 230, 232, 234, and 236 can include a relief. The relief at each of the edges 230, 232, 234, and 236 can be similar or different. For example, as shown in FIG. 5, a first relief 502 can have a rounded profile and a second relief 504 can have a chamfered profile.

Figure 6:
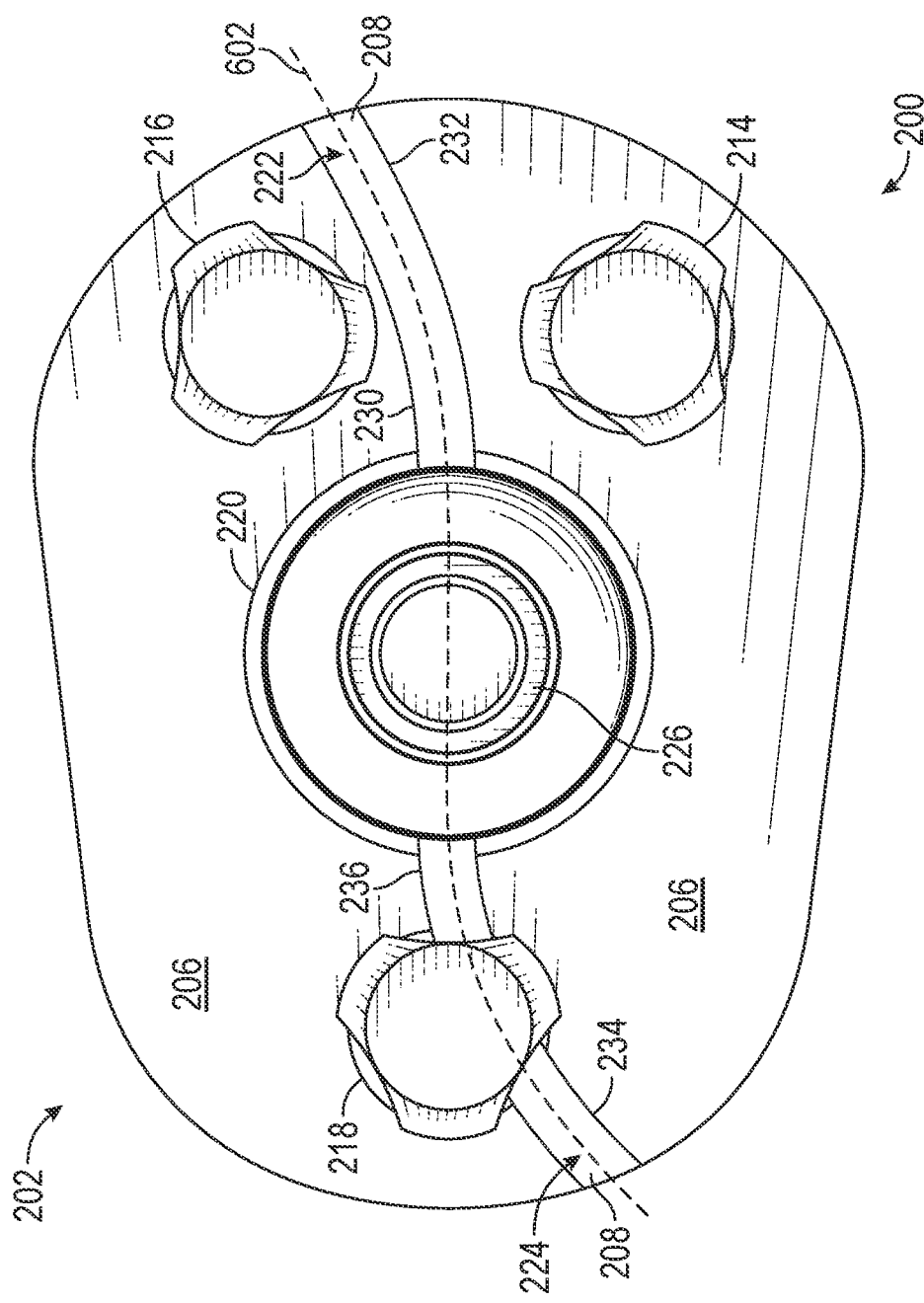
FIG. 6 shows a glenoid implant in accordance with at least one example of the present disclosure.

As shown in FIGS. 2A and 4, the groove 208 can follow a straight path 228 that divides the bone engaging surface 206. As shown in FIG. 6, the groove 208 can follow a curved path 602. The groove 208 can include both a straight portion and a curved portion. For example, a portion of the groove 208 passing between the first fixation peg 214 and the second fixation peg 216 can be straight as shown in FIGS. 2A and 4 and a portion of the groove 208 proximate the third fixation peg 218 can be curved as shown in FIG. 6. In other examples, the groove 208 can include one or more straight portions or one or more curved portions.

It should be noted that exemplary embodiments disclosed herein are directed to non-full wedge augments, but are rather directed to partial augments such as half augments. Further, it should be appreciated that the exemplary grooves disclosed herein, such as groove 208, are not formed as a result of fastener holes in the glenoid implant. In exemplary embodiments, groove 208 extends across the entire glenoid implant, and may or may not intersect separate fastener holes in the implant, but the groove is not formed by (or as a result of) such fastener holes.

Figure 11:
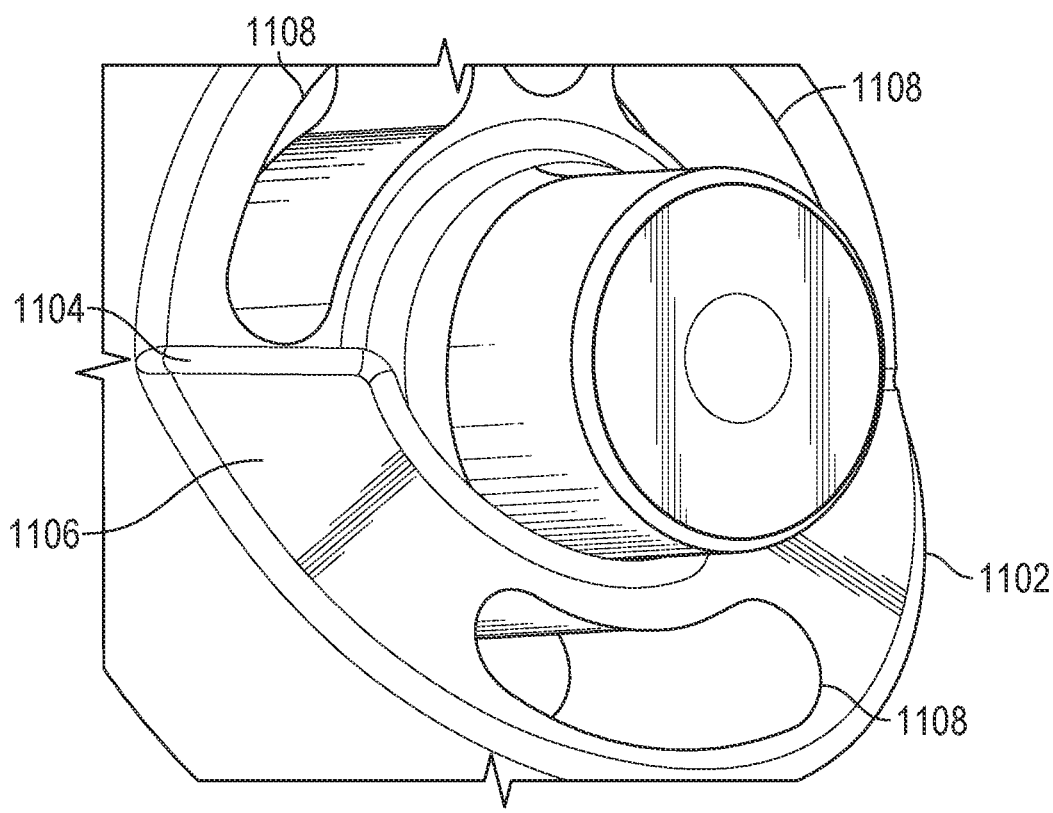
FIG. 11 shows a baseplate in accordance with at least one example of the present disclosure.
Figure 12:
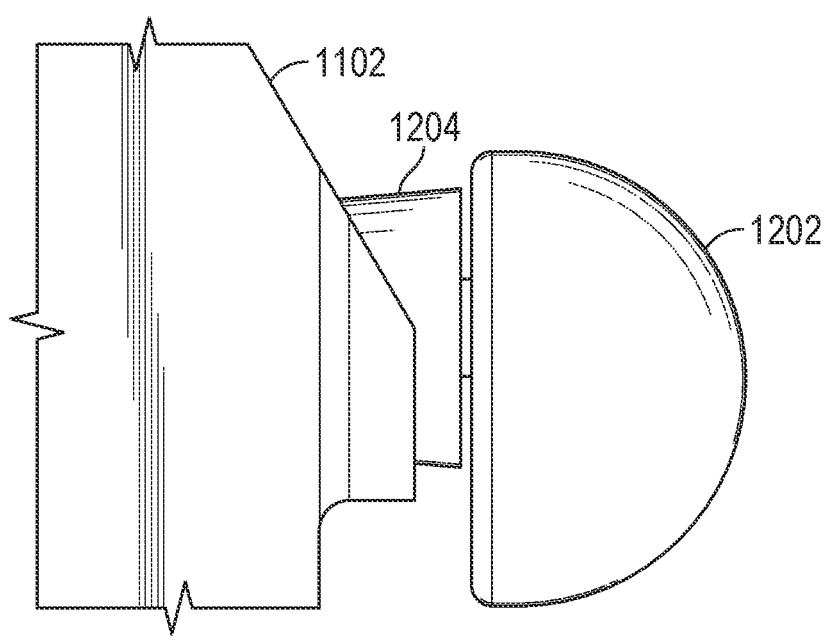
FIG. 12 shows a convex articulation surface in accordance with at least one example of the present disclosure.

FIGS. 2A-2C, 4, 6, and 8 generally show a glenoid implant 200 with a bone-engaging surface 206 and a concave articulation surface 204. Such a glenoid implant 200 is used in an anatomic or natural configuration where the humeral head (or an artificial articulating surface on the humeral side) articulates against a concave surface on the glenoid implant 200. It should be appreciated that the glenoid implant may also comprise a baseplate for use in a reverse configuration shoulder implant. In such a configuration, a convex articulation surface is implanted on the glenoid side, and a baseplate in one form or another is used to attach a bottom of the convex articulation surface to the glenoid bone. An exemplary baseplate 1102 and convex articulation surface 1202 are shown in FIGS. 11 and 12. The baseplate 1112 can comprise a groove 1104, similar to groove 208, and can serve a similar purpose as groove 208, such as to provide a location for irregularities on a vertex 114 to rest within the groove 1104 and allow the bone-engaging surface 1106 to better contact and sit flush against the bone surfaces 110 and 112. As shown in FIG. 12, the convex articulation surface 1202 can be attached to the baseplate 1112 via an augment 1204. The baseplate 1102 can include one or more mounting holes 1108. The mounting holes 1108 can be circular or oblong in shape.

Figure 7:
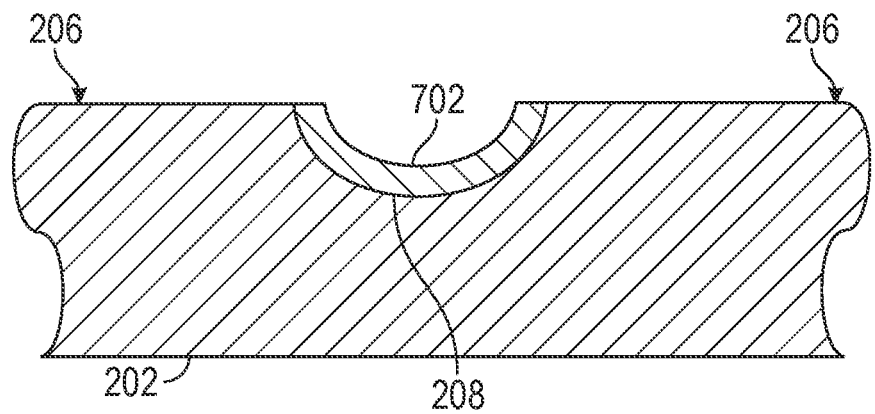
FIG. 7 shows a pours metal layer in accordance with at least one example of the present disclosure.

Referring to FIG. 7, the surface of the groove 208 can include a porous metal layer or insert 702. In addition, the bone-engaging surface 206 can also include a porous metal layer or be made of porous metal. Alternatively, groove 208 and bone-engaging surface 206 can be non-porous surfaces. The porous metal can allow for bone ingrowth to further secure the glenoid bone 200 to the glenoid. The porous metal layer can be a highly porous, three-dimensional metallic structure that can incorporate one or more of a variety of biocompatible metals such as, but not limited to, titanium, a titanium alloy, cobalt chromium, cobalt chromium molybdenum, tantalum, a tantalum alloy, niobium, or alloys of tantalum and niobium with one another or with other metals.

During surgery, a surgeon can apply bone cement or other adhesives to the groove 208. The bone cement or other adhesives can fill the space between the groove 208 and the irregularities at the vertex 114.

Figure 8:
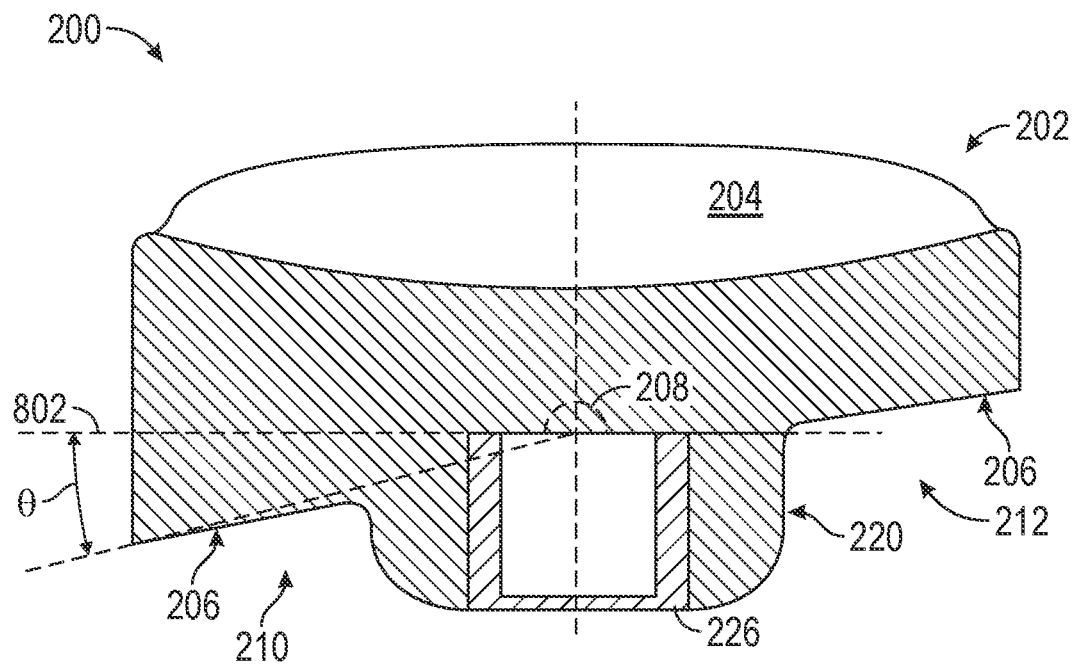
FIG. 8 shows a section view of a glenoid implant in accordance with at least one example of the present disclosure.

FIG. 8 shows a section view of the glenoid implant 200 in accordance with at least one example of the present disclosure. As shown in FIG. 8, the first section 210 of the bone engaging surface 206 can be positioned at an angle θ relative to a horizontal axis 802. The angle θ can vary from about 5 degrees to about 45 degrees, or more particularly, from about 10 degrees to about 20 degrees.

The angle θ can be patient-specific. In addition, the bone-engaging surface 206 can be patient-specific. For example, a surgeon can use X-ray or CT imaging to measure a geometry of a patient's glenoid. Using the measurements, the surgeon can order a patient-specific glenoid implant 200. The surgeon can also manufacture the glenoid implant 200 in the operating room using 3D printing technology.

The glenoid implant 200 can be manufactured from a variety of materials or combination of materials. For example, glenoid implant 200 can be manufactured from a polymer, metal, ceramic, or any combination thereof. For instance, the body 202 can be manufactured from a polymer, such as a vitamin F stabilized polyethylene, and the fixation pegs 214, 216, and 218 can be manufactured from a metal, such as surgical grade stainless steel or cobalt. Alternatively, the entire glenoid implant 200 can be made of a polymer.

The glenoid implant 200 can be manufactured using a variety of manufacturing methods such as, but not limited to, injection molding, machining, overmolding, etc. For example, the entire glenoid implant 200 can be injection molded from a polymer. In addition, the body 202 can be injection molded and the fixation pegs 214, 216, and 218 can be machined from a metal and press fitted into the body 202. In addition, the groove 208 can be machined into the body 202 after the body 202 is injection molded.

Figure 9:
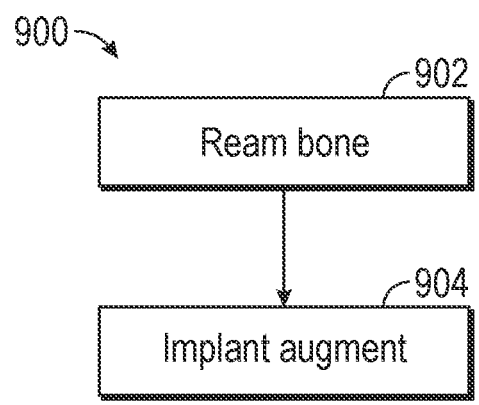
FIG. 9 shows an example method for a glenoid arthroplasty in accordance with at least one example of the present disclosure.
Figure 10:
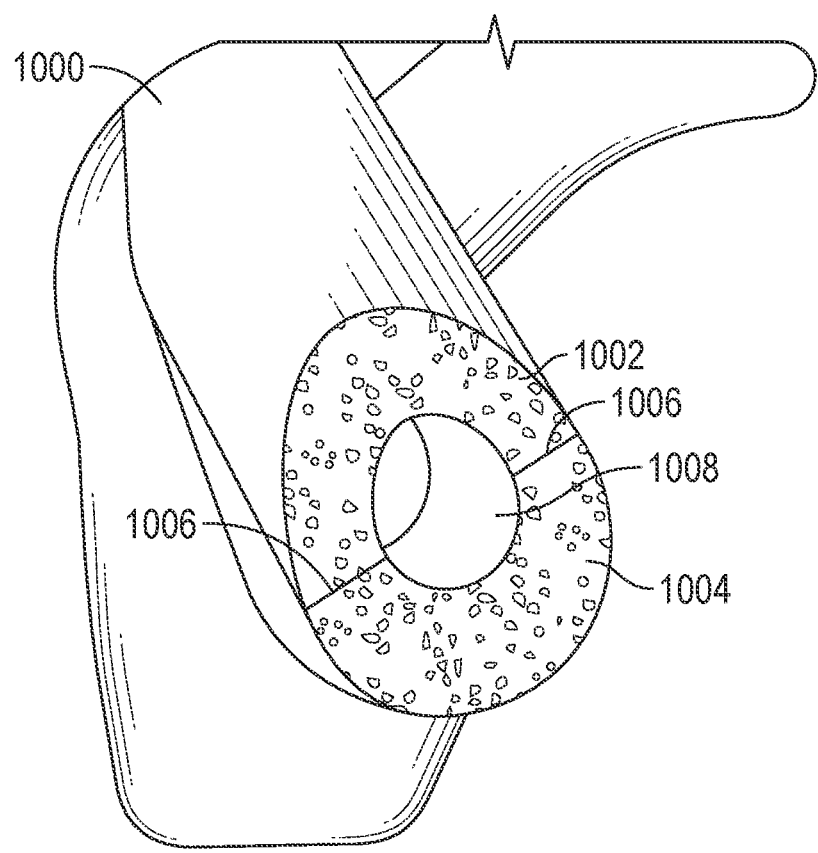
FIG. 10 shows a surgical site in accordance with at least one example of the present disclosure.

FIG. 9 shows a flowchart for a method 900 for glenoid arthroplasty in accordance with at least one example disclosed herein. The method 900 begins at stage 902 where a scapula 1000 can be reamed. For example, and as shown in FIG. 10, during surgery a surgeon can ream the scapula 1000 to define a first bone surface 1002 and a second bone surface 1004. The first bone surface 1002 and the second bone surface 1004 can define a vertex 1006 that might have one or more irregularities which can rest in groove 208. In addition to reaming the first bone surface 1002 and the second bone surface 1004, the surgeon can bore a socket 1008 into the scapula 1000 to receive the boss 220. Additional holes can be drilled for receiving two or three fixation pegs (e.g., 214, 216, 218).

From stage 902, the method 900 can proceed to stage 904 where the glenoid implant 200 can be implanted. For instance, the surgeon can press the boss 220 and fixation pegs 214, 216, 218 into their corresponding holes such that the first section 210 and the second section 212 of the bone-engaging surface 206 rest flush against the first bone surface 1002 and the second bone surface 1004 and the vertex 1006 and any corresponding irregularities rest within the groove 208, as disclosed herein. In addition, the surgeon can apply bone cement to one or more of the socket 1008, fixation pegs 214, 216, 218, the bone-engaging surface 206, the groove 208, etc.

As disclosed herein, a novel and inventive groove can be formed on the bone-engaging side of the glenoid implant to accommodate irregularities at a bone vertex that may arise as a result of imperfect reaming. Having irregularities reside within the groove provides some flexibility in reaming and preciseness in placing the glenoid implant by allowing the glenoid implant to sit flush on the prepared glenoid bone, thereby avoiding rocking and improper implantation of a glenoid implant.

It will be readily appreciated that while the groove has been disclosed for use on a glenoid implant, a similar groove may be formed on other implants where precise reaming is required to allow an implant to sit flush against the reamed bone.

It will be readily understood to those skilled in the art that various other changes in the details, material, and arrangements of the parts and method stages which have been described and illustrated in order to explain the nature of the inventive subject matter can be made without departing from the principles and scope of the inventive subject matter as expressed in the subjoined claims.

What is claimed is:

1. A glenoid implant, comprising:
   a body defining an articular surface and a bone-engaging surface opposite the articular surface, the bone-engaging surface defining only a single groove that separates a first section of the bone-engaging surface from a second section of the bone-engaging surface, the groove extending to a peripheral edge of the bone-engaging surface; and
   a plurality of fixation pegs extending from the bone-engaging surface,
   wherein:
   a fixation peg of the plurality of fixation pegs extends along a central axis;
   the fixation peg includes a cylindrical peg body that extends along the central axis;
   the fixation peg further includes a plurality of fixation elements that each protrude radially from the cylindrical peg body; and the central axis is a three-fold axis of rotational symmetry for each fixation element of the plurality of fixation elements.

2. The glenoid implant of claim 1, wherein the plurality of fixation pegs includes:
a first fixation peg disposed within and surrounded by the first section of the bone-engaging surface;
a second fixation peg disposed within and surrounded by the second section of the bone-engaging surface; and
a third fixation peg that intersects the groove.

3. The glenoid implant of claim 2, further comprising a boss extending from the bone-engaging surface, the boss dividing the groove into a first portion and a second portion, the third fixation peg intersecting the first portion of the groove.

4. The glenoid implant of claim 3, wherein the plurality of fixation pegs surrounds the boss.

5. The glenoid implant of claim 3, wherein the second portion of the groove is disposed between the first fixation peg and the second fixation peg.

6. The glenoid implant of claim 5, wherein:
the second portion of the groove defines a groove axis; and
the first fixation peg and the second fixation peg have respective central axes that are disposed in a plane that is substantially orthogonal to the groove axis.

7. The glenoid implant of claim 1, wherein the fixation elements are equally spaced along the central axis.

8. The glenoid implant of claim 1, wherein:
the fixation peg has a proximal end at the body and extends to a distal end away from the body; and
the fixation elements are located closer to the distal end than the proximal end.

9. The glenoid implant of claim 1, wherein the plurality of fixation elements includes three fixation elements.

10. The glenoid implant of claim 1, wherein the fixation pegs are formed from metal.

11. The glenoid implant of claim 1, wherein the fixation pegs are formed from at least one of surgical grade stainless steel and cobalt.

12. The glenoid implant of claim 1, wherein the fixation pegs are press fitted into the body.

13. The glenoid implant of claim 1, wherein the bone engaging surface is a distalmost surface of the body.

14. The glenoid implant of claim 1, wherein the articular surface and the bone engaging surface are farther apart in the first section of the bone engaging surface than in the second section of the bone engaging surface.

15. The glenoid implant of claim 1, wherein a thickness of the body defined between the articular surface and the bone engaging surface is greater along the first section of the bone engaging surface than along the second section of the bone engaging surface.

16. The glenoid implant of claim 1, wherein the first section of the bone engaging surface is angled with respect to the second section of the bone engaging surface.

17. A glenoid implant, comprising:
a body defining an articular surface and a bone-engaging surface opposite the articular surface, the bone-engaging surface defining only a single groove that separates a first section of the bone-engaging surface from a second section of the bone-engaging surface, the groove extending to a peripheral edge of the bone-engaging surface;
a boss extending from the bone-engaging surface, the boss dividing the groove into a first portion and a second portion;
a first fixation peg extending from the bone-engaging surface and disposed within the first section of the bone-engaging surface;
a second fixation peg extending from the bone-engaging surface and disposed within the second section of the bone-engaging surface; and
a third fixation peg extending from the bone-engaging surface and intersecting the first portion of the groove,
wherein:
the first fixation peg extends along a central axis;
the first fixation peg includes a cylindrical peg body that extends along the central axis;
the first fixation peg further includes a plurality of fixation elements that each protrude radially from the cylindrical peg body; and
the central axis is a three-fold axis of rotational symmetry for each fixation element of the plurality of fixation elements.

18. A glenoid implant, comprising:
a body defining an articular surface and a bone-engaging surface opposite the articular surface, the bone-engaging surface defining only a single groove that separates a first section of the bone-engaging surface from a second section of the bone-engaging surface, the groove extending to a peripheral edge of the bone-engaging surface;
a first fixation peg extending from the bone-engaging surface and disposed within the first section of the bone-engaging surface;
a second fixation peg extending from the bone-engaging surface and disposed within the second section of the bone-engaging surface;
a third fixation peg extending from the bone-engaging surface and intersecting the groove, the third fixation peg extending along a central axis; and
a boss extending from the bone-engaging surface, the boss dividing the groove into a first portion and a second portion, the boss configured to accept a removable central peg,
wherein:
the third fixation peg includes a cylindrical peg body that extends along the central axis;
the third fixation peg further includes a plurality of fixation elements that each protrude radially from the cylindrical peg body; and
the central axis is a three-fold axis of rotational symmetry for each fixation element of the plurality of fixation elements.

* * * * *

UNITED STATES PATENT AND TRADEMARK OFFICE
CERTIFICATE OF CORRECTION

| | |
|---|---|
| PATENT NO. | : 12,220,321 B2 |
| APPLICATION NO. | : 17/975767 |
| DATED | : February 11, 2025 |
| INVENTOR(S) | : Kehres et al. |

Page 1 of 1

It is certified that error appears in the above-identified patent and that said Letters Patent is hereby corrected as shown below:

On the Title Page

On page 2, in Column 2, item (56) under "Other Publications", Line 1, delete "malled" and insert --mailed-- therefor Signed and Sealed this
First Day of April, 2025

Coke Morgan Stewart
*Acting Director of the United States Patent and Trademark Office*